(12) United States Patent
Ascheman

(10) Patent No.: US 6,503,218 B1
(45) Date of Patent: Jan. 7, 2003

(54) ANKLE BRACE

(76) Inventor: James M. Ascheman, 1908 Ridgewood Ave., White Bear Lake, MN (US) 55110

( * ) Notice: Subject to any disclaimer, the term of this patent is extended or adjusted under 35 U.S.C. 154(b) by 0 days.

(21) Appl. No.: 09/806,367

(22) PCT Filed: Sep. 30, 1999

(86) PCT No.: PCT/US99/22554

§ 371 (c)(1),
(2), (4) Date: Mar. 28, 2001

(87) PCT Pub. No.: WO00/18348

PCT Pub. Date: Apr. 6, 2000

(51) Int. Cl.[7] ................................................. A61F 5/00
(52) U.S. Cl. ........................................... 602/23; 602/27
(58) Field of Search .............................. 602/5, 23, 26, 602/27; 128/869, 882

(56) References Cited

U.S. PATENT DOCUMENTS

| 4,523,394 A | 6/1985 | Lindh et al. | 36/89 |
|---|---|---|---|
| 4,753,229 A | 6/1988 | Sutherland | 128/80 H |
| 4,865,023 A | 9/1989 | Craythorne et al. | 128/80 |
| 4,922,630 A | 5/1990 | Robinson | 36/89 |
| 4,936,295 A | 6/1990 | Crane | 128/80 H |
| 5,445,602 A | 8/1995 | Grim et al. | 602/27 |
| 5,792,087 A | 8/1998 | Pringle | 602/27 |

*Primary Examiner*—Michael A. Brown
(74) *Attorney, Agent, or Firm*—Michael S. Sherrill

(57) ABSTRACT

This invention is an in-the-shoe ankle brace (10) including a girth (21), an adjustable fastener (25) attached to the lateral ends of the girth (21), an ankle bone cover (30) extending downward from the girth (21) with at least a portion of the cover positioned proximate the first lateral end of the girth, at least one strap (42) extending downward from the girth (21) having a first end (42a) attached to the girth (21) proximate the first lateral end of the girth (21), a second end (42b) attached to the girth (21) proximate the second lateral end of the girth (21) so as to define a carriage extending below the girth (21), and a heel pad (50) attached to the strap within the carriage.

14 Claims, 2 Drawing Sheets

ANKLE BRACE

FIELD OF THE INVENTION

The invention relates to ankle braces. More particularly, the invention relates to devices for protecting ankle ligaments against injury resulting from hyperinversion or hypereversion of the foot relative to the ankle.

BACKGROUND

The ankle joint permits two types of pivotal movement of the talus or ankle bone about the leg bone, namely a generally up and down pivotal movement of the foot within the plane of the leg bone, commonly referred to as dorsiflexion and plantarflexion, and side-to-side pivotal movement of the foot relative to the ankle, commonly referred to as inversion and eversion. As is well known, excessive inversion ("hyperinversion") and excessive eversion ("hypereversion") of the foot can damage the ligaments at the ankle joint and cause ankle sprain which is a painful and sometimes debilitating injury.

One commonly used technique for reducing the possibility of ankle sprain or reinjury of a sprained ankle is to wrap tape tightly around the ankle joint to partially restrict movement of the foot about the leg. While somewhat effective for supporting the ankle against hyperinversion and hypereversion (hereinafter collectively referenced as "hyperversion"), this technique has proven to be of limited value in preventing hyperversion. In addition, the technique has not gained widespread acceptance as it is time consuming to apply the tape at frequent intervals and is often uncomfortable and irritating to the wearer.

Accordingly, a wide variety of mechanical or orthopedic appliances have been designed to protect the foot against undesirable movement during rehabilitation. Theses braces are generally quite bulky and permit only limited movement of the foot. Such rehabilitation braces are not designed for use during a physical activity. Typical examples of such rehabilitation braces are disclosed in Crispin, U.S. Pat. No. 4,771,768 and Young, U.S. Pat. No. 5,429,588.

Other, sports braces have been designed primarily to prevent injury or reinjury of the ankle by restricting movement of the foot about the leg at the ankle joint while still permitting a range of movement sufficient to allow the wearer to participate in athletics. These ankle braces are sometimes designed to be worn inside the shoe of the wearer while others are designed to be worn outside the shoe.

Ankle braces designed for use inside the shoe of the wearer are generally preferred as they do not require use of a customized shoe, require modification of the shoe to accommodate attachment of the brace to the side of the shoe, nor interfere with traction due passage of a strap member underneath the shoe. However, in order to provide sufficient bracing against the substantial forces encountered at the ankle joint during normal athletic activity, in-the-shoe braces tend to be too bulky, heavy, and/or restrictive for routine use during athletic activity. Furthermore, such in-the-shoe braces tend to be uncomfortable and result in rubbing and chaffing of the ankle as they are designed to be worn tightly against the ankle and tend to be pressed even tighter against the ankle and foot by athletic shoes which are generally designed to conform as closely as possible to the shape of the foot.

Efforts to design a light and comfortable in-the-shoe ankle brace tend to result in ankle braces which are not sturdy enough to withstand the large forces that act upon the components of the brace.

It is well understood that some inversion and eversion movement of the ankle is necessary to permit effective athletic activity. Excessive restriction of the inversion and eversion of the ankle tends to interfere with such athletic actions as planting a foot to change direction or maintaining balance on uneven ground. While some braces permit limited inversion or eversion movement, they tend to require a complicated and time consuming routine in order to apply and adjust the brace.

Accordingly, there is a need for an easy to use, inexpensive and comfortable in-the-shoe ankle brace that freely permits a normal range of movement of the foot at the ankle joint while simultaneously preventing hyperversion.

SUMMARY OF THE INVENTION

Figures 1, 2:
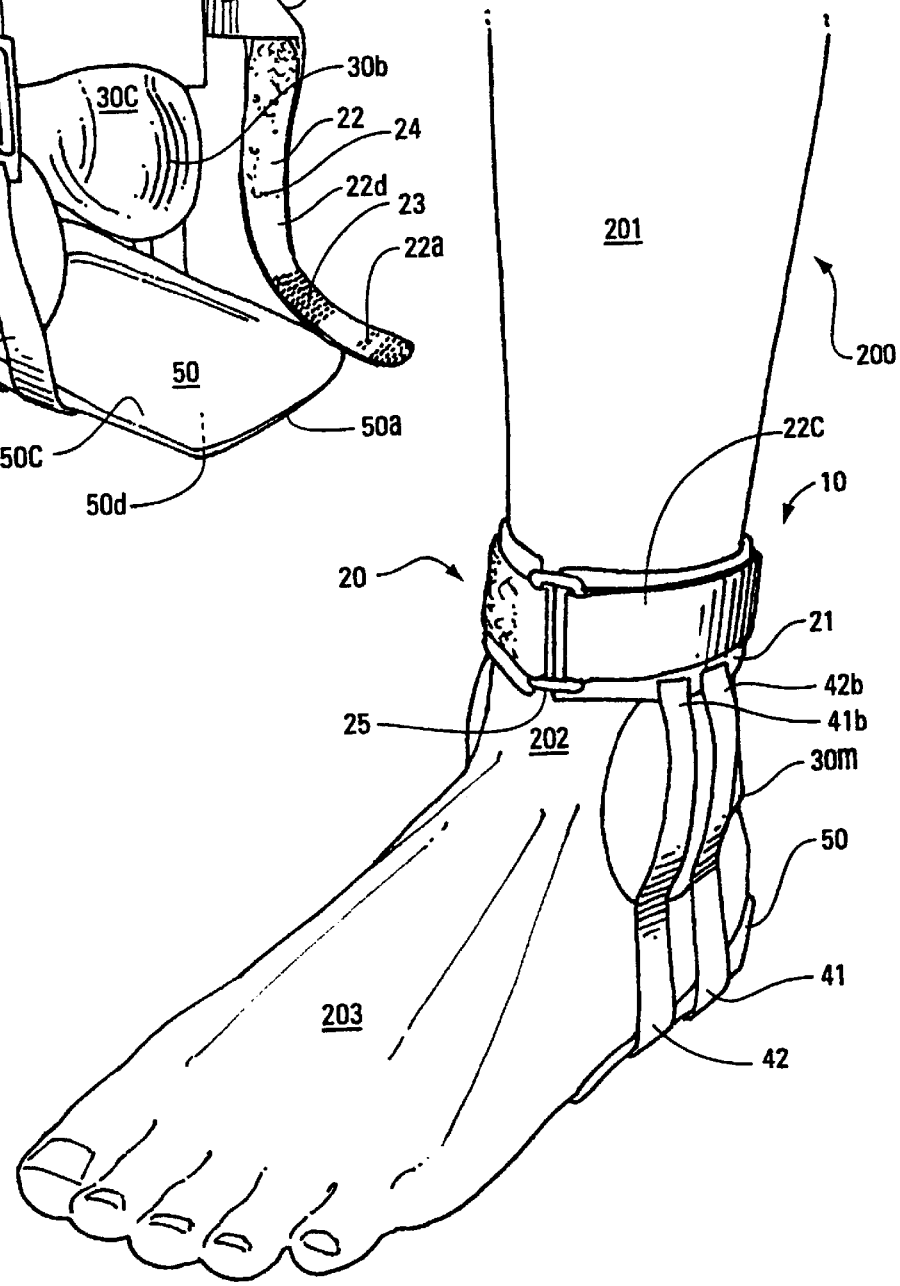
FIG. 1 is a perspective view of a first embodiment of the invention.
FIG. 2 is a perspective view of the embodiment of the invention shown in FIG. 1 worn on a foot.

The in-the-shoe ankle brace includes (a) a girth, (b) an adjustable fastening means attached to the lateral ends of the girth, (c) an ankle bone cover extending from the lower longitudinal edge of the girth with a portion of the cover positioned proximate the first lateral end of the girth, (d) at least one strap, preferably two, extending from the lower longitudinal edge of the girth and having (i) a first end attached to the girth proximate the first lateral end of the girth, and (ii) a second end attached to the girth proximate the second lateral end of the girth so as to define a carriage extending from the girth, and (e) a heel pad attached to the strap within the carriage.

Construction of the in-the-shoe brace may alternatively be described relative to the anatomy of an ankle. When described in this fashion, the brace includes (a) a girth, (b) an adjustable fastening means cooperatively attached to the girth for releasably encircling the girth around the lower leg of a wearer when fastened, (c) an ankle bone cover cooperatively attached to the girth so as to be effective for covering at least one end of an ankle bone of a wearer when the brace is worn, (d) at least one strap, preferably two, having a first end attached to the girth at a first point and a second end attached to the girth at a second point wherein (i) the first and second points are substantially diametrically opposed proximate opposite ends of an ankle bone of a wearer when the brace is worn, and (ii) the strap defines a carriage extending from the girth, and (e) a heel pad cooperatively attached to the strap within the carriage.

DETAILED DESCRIPTION OF THE INVENTION INCLUDING A BEST MODE

Nomenclature

| | |
|---|---|
| 10 | Ankle Brace (First Embodiment) |
| 20 | Girth |
| 21 | Base Member |

-continued

| | |
|---|---|
| 21a | First End of Base Member |
| 21b | Second End of Base Member |
| 21c | Inner Surface of Base Member |
| 21d | Outer Surface of Base Member |
| 22 | Strap |
| 22a | Distal End of Strap |
| 22b | Proximal End of Strap |
| 22c | Inner Surface of Strap |
| 22d | Outer Surface of Strap |
| 23 | Hooked Portion of Outer Surface of Strap |
| 24 | Looped Portion of Outer Surface of Strap |
| 25 | Ring |
| 30 | Ankle Bone Cover |
| 30a | First Ankle Cup Defined by Ankle Cover |
| 30b | Second Ankle Cup Defined by Ankle Cover |
| 30c | Inner Surface of Ankle Cover |
| 30d | Outer Surface of Ankle Cover |
| 30m | Intermediate Connecting Member |
| 41 | First Strap |
| 41a | First End of First Strap |
| 41b | Second End of First Strap |
| 42 | Second Strap |
| 42a | First End of Second Strap |
| 42b | Second End of Second Strap |
| 50 | Heel Pad |
| 50a | Forward End of Heel Pad |
| 50b | Rearward End of Heel Pad |
| 50c | Inner Surface of Heel Pad |
| 50d | Outer Surface of Heel Pad |
| 100 | Ankle Brace (Second Embodiment) |
| 120 | Girth |
| 121 | Base Member |
| 121a | First End of Base Member |
| 121b | Second End of Base Member |
| 121c | Inner Surface of Base Member |
| 121d | Outer Surface of Base Member |
| 122 | Strap |
| 122a | Distal End of Strap |
| 122c | Inner Surface of Strap |
| 122d | Outer Surface of Strap |
| 125 | Ring |
| 130 | Ankle Bone Cover |
| 130a | First Ankle Cup Defined by Ankle Cover |
| 130b | Second Ankle Cup Defined by Ankle Cover |
| 130c | Inner Surface of Ankle Cover |
| 130d | Outer Surface of Ankle Cover |
| 130m | Intermediate Connecting Member |
| 141 | First Strap |
| 141a | First End of First Strap |
| 142 | Second Strap |
| 142a | First End of Second Strap |
| 142b | Second End of Second Strap |
| 150 | Heel Pad |
| 150a | Forward End of Heel Pad |
| 150b | Rearward End of Heel Pad |
| 150c | Inner Surface of Heel Pad |
| 150d | Outer Surface of Heel Pad |
| 160 | Lateral Restraining Band |
| 161 | Selected Points of Attachment |
| 162 | First Channel |
| 163 | Second Channel |
| 200 | Wearer |
| 201 | Leg of Wearer |
| 202 | Ankle of Wearer |
| 203 | Foot of Wearer |

Construction

First Embodiment

A first embodiment of the invention, shown in FIGS. 1 and 2, is an ankle brace 10 including (i) an adjustable ankle girth 20, (ii) an ankle bone cover 30 attached to and extending downward from the ankle girth 20, (iii) a pair of straps 41 and 42 with the ends 41a, 41b and 42a, 42b of each strap 41 and 42 diametrically attached to the ankle girth 20, and (iv) a heel pad 50 suspended a fixed distance below the ankle girth 20 by the straps 41 and 42.

Ankle Girth 20

The ankle brace 10 includes an adjustable ankle girth 20. The ankle girth 20 includes a base member 21 having a lateral length (unnumbered) sufficient to extend substantially completely around the leg 201 of a wearer 200 just above the ankle 202 when the ankle brace 10 is properly fitted onto the leg 201. The base member 21 is preferably constructed from or lined on the inner surface 21c with a soft, conformable and absorbent material, such as cotton, so that the ankle brace 10 may be worn directly upon the ankle 202 of a wearer 200 without the need for any intervening article of clothing, such as a sock (not shown).

A laterally extending strap 22 extends from the second end 21b of the base member 21. A ring 25 configured and arranged to accept passage of the distal end 22a of the strap 22 therethrough is secured to the first end 21a of the base member 21. The outer surface 22d of the strap 22 has a looped surface 24 along substantially the entire length of the strap 22 except for the distal end 22a of the strap 22 which has a hooked surface 23 effective for bonding with the looped surface 24 upon contact. Such hook and loop configuration of the strap 22 allows the ankle brace 10 to be quickly and easily applied, adjusted and removed by simply (i) passing the distal end 22a of the strap 22 through the ring 25, (ii) pulling the distal end 22a of the strap 22 back towards the proximal end 22b of the strap until the base member 21 is snug against the leg 201 of the wearer 200, and (iii) pressing the hooked portion 23 of the strap 22 into contact with the looped portion 24 of the strap 22. The strap 22 and ring 25 are preferably secured to the outer surface 21d of the base member 21 in such a manner that they will not contact the skin (unnumbered) of a wearer 200 during normal use and thereby increase the comfort of the brace 10.

Of course, those skilled in the art would readily recognize the ability to select from the numerous other releasable fastening means effective for adjustably securing the base member 21 around the lower leg 201 of a wearer 200, including specifically, but not exclusively buttons, a belt buckle, a clamp, eyelets, pawl and ratchet system, snaps, etc.

Ankle Bone Cover 30

As shown in FIGS. 1 and 2, an ankle bone cover 30 is attached to and extends downward from the ankle girth 20. The ankle bone cover 30 includes first 30a and second 30b ankle cups configured and arranged to cover the protruding ankle bone (unnumbered) on each side of the ankle 202. The inner surfaces 30c of the ankle cups 30a and 30b are preferably concave in shape so as to accommodate the protruding ankle bone (unnumbered) and thereby reduce any tendency of the brace 10 to slip during use. The ankle bone cover 30 shown in FIGS. 1 and 2 provides both ankle cups 30a and 30b formed from a single continuous piece of material with an intermediate connecting member 30m configured and arranged to extend around and cover the back of the ankle 202. Alternatively, the ankle cups 30a and 30b may be provided as separate elements.

The ankle bone cover 30 is preferably constructed with a soft inner surface 30c and an abrasion resistant outer surface 30d. A soft inner surface 30c allows the ankle brace 10 to be worn directly upon the ankle 202 of a wearer 200 without the need for any intervening article of clothing, such as a sock (not shown). An abrasion resistant outer surface 30d is desired as the ankle bone cover 30 will typically be positioned at least partially within the shoe (not shown) of the wearer 200 such that the outer surface 30d will rub against the inside surface of the shoe (not shown) during normal use. Suitable materials include the various foamed plastics, such a polyurethane foam with or without a lining, such as a cotton fabric, laminated to the inner surface and/or a protective layer, such as a polyvinyl chloride shell, laminated to the outer surface.

The ankle bone cover 30 preferably has a thickness of between about 0.125 to 0.25 inches (about 0.318 to 0.635 cm) for purposes of increasing the lateral distance between straps 41 and 42 and the pivot point of the ankle 202. By providing the ankle bone cover 30 with such a thickness and positioning the straps 41 and 42 over the ankle bone cover 30, the lateral distance between straps 41 and 42 and the pivot point of the ankle 202 is increased. This distancing produces meaningful leverage for the straps 41 and 42 (i.e., small rotational changes at the ankle joint translate to substantial movement of the straps 41 and 42) so that less precision is required in the length of the straps 41 and 42 to insure that straps 41 and 42 are engaged shortly before reaching the point of hyperversion.

Straps 41 and 42

As shown in FIGS. 1 and 2, straps 41 and 42 form a U-shaped carriage below the girth 20 with a first end 41a and 42a of each strap 41 and 42 secured (e.g, sewn or adhesively bonded) proximate the first end 21a of the base member 21 and a second end 41b and 42b of each strap 41 and 42 secured (e.g., sewn) proximate the second end 21b of the base member 21. Such an attachment of the straps 41 and 42 results in a diametric positioning of the ends of each strap 41a, 41b and 42a, 42b when the brace 10 is worn.

The straps 41 and 42 extend longitudinally over the outer surface 30d of the ankle bone cover 30 at the ankle cups 30a and 30b. The straps 41 and 42 may be attached to the outer surface 30d of the ankle bone cover 30 by a suitable fastening means (e.g., sewn or adhesively bonded) but are preferably allowed to slide freely in at least the longitudinal direction over the ankle bone cover 30 so as to prevent shifting of the ankle bone cover 30 as the straps 41 and 42 move during normal use of the brace 10.

The straps 41 and 42 may be independently constructed from substantially any material capable of withstanding the normal forces to which the straps 41 and 42 will be exposed during normal use. Generally, inextensible and modestly extensible (i.e., limited strechability when subjected to high normal pulling force) materials are preferred (e.g., woven nylon, high durometer rubber, etc) as highly extensible materials (e.g., spandex) will not provide sufficient support against hyperversion.

The straps 41 and 42 need not include a means for adjusting the length of the straps 41 and 42. Such adjustment is not necessary for proper functioning of the brace 10 as proper longitudinal positioning of the brace 10 can be accommodated by properly positioning the girth 20 on the leg 201 of a wearer 200. In addition, for reasons explained in detail later in this disclosure, exact precision in longitudinal positioning of the brace 10 is not required to achieve the desired protection against hyperversion.

While FIGS. 1 and 2 show two continuous straps 41 and 42, various alternatives may also be employed, including additional straps (e.g., three straps), chords rather than straps, strap halves wherein the second end of each strap half is attached to the heel pad 50, etc.

Heel Pad 50

As shown in FIGS. 1 and 2, a heel pad 50 is cradled within the U-shaped carriage formed by the straps 41 and 42. The heel pad 50 is configured and arranged to comfortably fit within typical athletic shoes (not shown). The heel pad 50 is tapered from back 50b to front 50a with the inner surface 50c shaped to conform to the contours of the heel (unnumbered). The straps 41 and 42 are attached (e.g., sewn or adhesively bonded) to the outer surface 50d of the heel pad 50 so as to prevent the straps 41 and 42 from slipping left to right between the heel pad 50 and the shoe (not shown) during use. Such slipping would decrease the support offered by the brace 10 as the length of the straps 41 and/or 42 on the side requiring support would tend to increase at the very time that support against hyperversion is desired.

The heel pad 50 is preferably constructed from a soft yet abrasion resistant material. Suitable materials include any of the various materials commonly used for shoe inserts, including foamed plastics, such a polyurethane foam, with or without a lining on the inner surface 50c.

Second Embodiment

Figure 3:
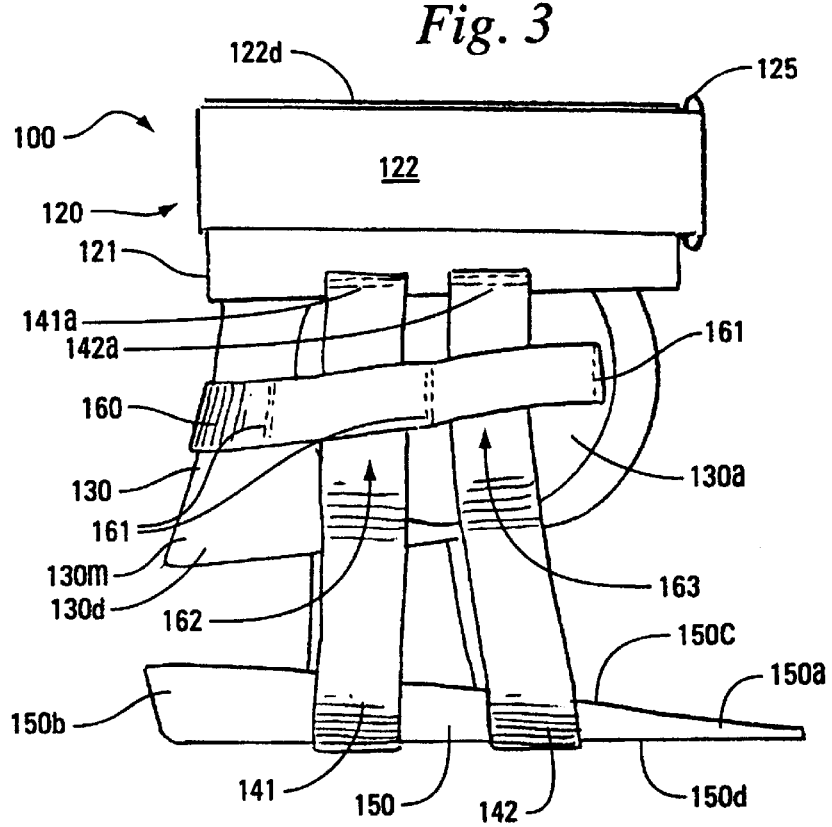
FIG. 3 is a side-view of a second embodiment of the invention.
Figure 4:
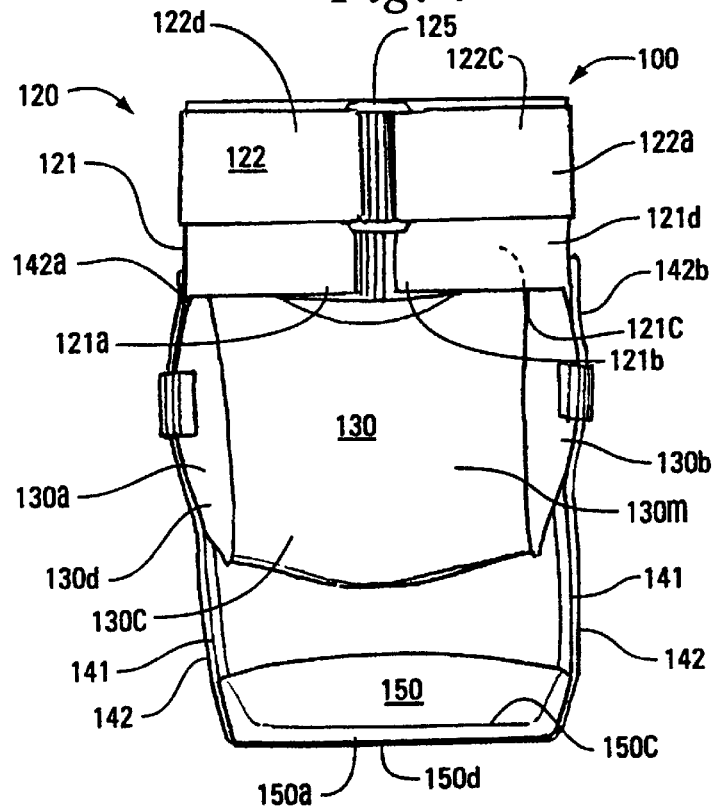
FIG. 4 is a front view of the invention shown in FIG. 3.

A second embodiment of the invention, shown in FIGS. 3 and 4, is an ankle brace 100 including (i) an adjustable ankle girth 120, (ii) an ankle bone cover 130 attached to and extending downward from the ankle girth 120, (iii) a pair of straps 141 and 142 with the ends 141a, 141b and 142a, 142b of each strap 141 and 142 diametrically attached to the ankle girth 120, (iv) a heel pad 150 suspended a fixed distance below the ankle girth 120 by the straps 141 and 142, and (v) a lateral restraining band 160 attached to each of the ankle cups 130a and 130b at selected points 161 positioned on either side of the straps 141 and 142 so as to limit lateral movement of the straps 141 and 142 without significantly interfering with longitudinal movement of the straps 141 and 142.

Ankle Girth 120

The ankle brace 100 includes an adjustable ankle girth 120. The ankle girth 120 includes a base member 121 having a lateral length (unnumbered) sufficient to extend substantially completely around the leg 201 of a wearer 200 just above the ankle 202 when the ankle brace 100 is properly fitted onto the leg 201. The base member 121 is preferably constructed from or lined on the inner surface 121c with a soft, conformable and absorbent material, such as cotton, so that the ankle brace 100 may be worn directly upon the ankle 202 of a wearer 200 without the need for any intervening article of clothing, such as a sock (not shown).

A laterally extending strap 122 extends from the second end 121b of the base member 121. A ring 125 configured and arranged to accept passage of the distal end 122a of the strap 122 therethrough is secured to the first end 121a of the base member 121. The outer surface 122d of the strap 122 has a looped surface (not shown) along substantially the entire length of the strap 122 except for the distal end 122a of the strap 122 which has a hooked surface (not shown) effective for bonding with the looped surface (not shown) upon contact. Such hook and loop configuration of the strap 122 allows the ankle brace 100 to be quickly and easily applied, adjusted and removed by simply (i) passing the distal end 122a of the strap 122 through the ring 125, (ii) pulling the distal end 122a of the strap 122 back towards the proximal end (not shown) of the strap 122 until the base member 121 is snug against the leg 201 of the wearer 200, and (iii) pressing the hooked portion (not shown) of the strap 122 into contact with the looped portion (not shown) of the strap 122. The strap 122 and ring 125 are preferably secured to the outer surface 121d of the base member 121 in such a manner that they will not contact the skin (unnumbered) of a wearer 200 during normal use and thereby increase the comfort of the brace 100.

Of course, those skilled in the art would readily recognize the ability to select from the numerous other releasable fastening means capable of adjustably securing the base member 121 around the lower leg 201 of a wearer 200, including specifically, but not exclusively buttons, a belt buckle, a clamp, eyelets, pawl and ratchet system, snaps, etc.

Ankle Bone Cover 130

As shown in FIGS. 3 and 4, an ankle bone cover 130 is attached to and extends downward from the ankle girth 120. The ankle bone cover 130 includes first 130a and second 130b ankle cups configured and arranged to cover the protruding ankle bone (unnumbered) on each side of the ankle 202. The inner surfaces 130c of the ankle cups 130a and 130b are preferably concave in shape so as to accommodate the protruding ankle bone (unnumbered) and thereby reduce any tendency of the brace 100 to slip during use. The ankle bone cover 130 shown in FIGS. 3 and 4 provides both ankle cups 130a and 130b formed from a single continuous piece of material with an intermediate connecting member 130m configured and arranged to extend around and cover the back of the ankle 202. The intermediate connecting member 130m is also shaped so as to extend downward a distance sufficient to insure that the lower portion (unnumbered) of the intermediate connecting member 130m will be positioned within the shoe (not shown) of a wearer 200 during normal use so as to further reduce any tendency of the brace 100 to shift during use. The ankle cups 30a and 30b may alternatively be provided as separate elements.

The ankle bone cover 130 is preferably constructed with a soft inner surface 130c and an abrasion resistant outer surface 130d. A soft inner surface 130c allows the ankle brace 100 to be worn directly upon the ankle 202 of a wearer 200 without the need for any intervening article of clothing, such as a sock (not shown). An abrasion resistant outer surface 130d is desired as the ankle bone cover 130 will typically be positioned at least partially within the shoe (not shown) of the wearer 200 such that the outer surface 130d will rub against the inside surface of the shoe (not shown) during normal use. Suitable materials include the various foamed plastics, such a polyurethane foam with or without a lining, such as a cotton fabric, laminated to the inner surface and/or a protective layer, such as a polyvinyl chloride shell, laminated to the outer surface.

The ankle bone cover 130 preferably has a thickness of between about 0.125 to 0.25 inches (about 0.318 to 0.635 cm) for purposes of increasing the lateral distance between straps 141 and 142 and the pivot point of the ankle 202. By providing the ankle bone cover 130 with such a thickness and positioning the straps 141 and 142 over the ankle bone cover 130, the lateral distance between straps 141 and 142 and the pivot point of the ankle 202 is increased. This distancing produces meaningful leverage for the straps 141 and 142 (i.e., small rotational changes at the ankle joint translate to substantial movement of the straps 141 and 142) so that less precision is required in the length of the straps 141 and 142 to insure that straps 141 and 142 are engaged shortly before reaching the point of hyperversion.

Straps 141 and 142

As shown in FIGS. 3 and 4, straps 141 and 142 form a U-shaped carriage below the girth 120 with a first end 141a and 142a of each strap 141 and 142 secured (e.g., sewn or adhesively bonded) proximate the first end 121a of the base member 121 and a second end (not shown) and 142b of each strap 141 and 142 secured (e.g., sewn) proximate the second end 121b of the base member 121. Such an attachment of the straps 141 and 142 results in a diametric positioning of the ends of each strap 141a, 141b and 142a, 142b when the brace 100 is worn.

The straps 141 and 142 extend longitudinally over the outer surface 130d of the ankle bone cover 130 at the ankle cups 130a and 130b. The straps 141 and 142 are not attached to the outer surface 130d of the ankle bone cover 130. The straps 141 and 142 are allowed to slide freely in at least the longitudinal direction over the ankle bone cover 130 so as to prevent shifting of the ankle bone cover 130 as the straps 141 and 142 move during normal use of the brace 100.

The straps 141 and 142 may be independently constructed from substantially any material capable of withstanding the normal forces to which the straps 141 and 142 will be exposed during normal use. Generally, inextensible and modestly extensible (i.e., limited strechability when subjected to high normal pulling force) materials are preferred (e.g., woven nylon, high durometer rubber, etc) as highly extensible materials (e.g., spandex) will not provide sufficient support against hyperversion.

The straps 141 and 142 need not include a means for adjusting the length of the straps 141 and 142. Such adjustment is not necessary for proper functioning of the brace 100 as proper longitudinal positioning of the brace 100 can be accommodated by properly positioning the girth 120 on the leg 201 of a wearer 200. In addition, for reasons explained in detail later in this disclosure, exact precision in longitudinal positioning of the brace 100 is not required to achieve the desired protection against hyperversion.

While FIGS. 3 and 4 show two continuous straps 141 and 142, various alternatives may also be employed, including additional straps (e.g., three straps), chords rather than straps, strap halves wherein the second end of each strap half is attached to the heel pad 150, etc.

Heel Pad 150

As shown in FIGS. 3 and 4, a heel pad 150 is cradled within the U-shaped carriage formed by the straps 141 and 142. The heel pad 150 is configured and arranged to comfortably fit within typical athletic shoes (not shown). The heel pad 150 is tapered from back 150b to front 150a with the inner surface 150c shaped to conform to the contours of the heel (unnumbered). The straps 141 and 142 are attached (e.g., sewn or adhesively bonded) to the outer surface 150d of the heel pad 150 so as to prevent the straps 141 and 142 from slipping left to right between the heel pad 150 and the shoe (not shown) during use. Such slipping would decrease the support offered by the brace 100 as the length of the straps 141 and/or 142 on the side requiring support would tend to increase at the very time that support against hyperversion is desired.

The heel pad 150 is preferably constructed from a soft yet abrasion resistant material. Suitable materials include any of the various materials commonly used for shoe inserts, including foamed plastics, such a polyurethane foam, with or without a lining on the inner surface 150c.

Heel Pad 150

As shown in FIGS. 3 and 4, a lateral restraining band 160 is attached (e.g., sewn or adhesively bonded) to the outer surface 130d of each of the ankle cups 130a and 130b at selected points 161 positioned on either side of the straps 141 and 142 so as to form a first 162 and second 163 channels through which straps 141 and 142 pass, respectively. Passage of the straps 141 and 142 through the channels 162 and 163 formed by the lateral restraining band 160 is effective for limiting lateral movement of the straps 141 and 142 without significantly interfering with longitudinal movement of the straps 141 and 142.

The lateral restraining band 160 can be conveniently constructed from the same material used for the straps 141 and 142.

Use

For purposes of convenience only, use of the ankle brace 10, 100 shall be described in connection with the first embodiment, FIGS. 1 and 2, as use of both embodiments described herein is essentially the same.

The ankle brace 10 may be quickly and easily put-on by simply (i) holding the girth 20 open with both hands, (ii) placing the heel (unnumbered) of the foot 203 onto the heel pad 50 with the lower leg 201, ankle 202 and foot 203 positioned within the open carriage formed by the straps 41 and 42, (iii) fastening the strap 22 around the lower leg 201, and (iv) adjusting the position of the ankle cups 30a and 30b directly over the ankle bones (unnumbered) if necessary.

The ankle brace 10 allows substantially unrestricted dorsiflexion and plantarflexion movement of the foot 203. The ankle brace 10 also allows substantially unrestricted inversion and eversion movement of the foot 203 until the extension limits of straps 41 and 42, governed by the amount of slack provided in the straps 41 and 42 and/or the extensibility of the straps 41 and 42, at which time continued inversion or eversion is restricted by the brace 10.

I claim:

1. An in-the-shoe ankle brace, comprising:
   (a) a girth having first and second lateral ends;
   (b) an adjustable fastening means cooperatively attached to the girth effective for releasably encircling the girth around a lower leg of a wearer when fastened;
   (c) an ankle cover cooperatively attached to the girth so as to be effective for covering at least one end of a malleolus of a wearer when the brace is worn;
   (d) a first strap and a second strap configured and arranged so as to be substantially parallel with each other, each strap having a first end attached to the girth at a first point and a second end attached to the girth at a second point wherein (i) the first and second points are positioned above the malleolus of a wearer when the brace is worn, (ii) the first and second points are substantially diametrically opposed proximate opposite ends of the malleolus of a wearer when the brace is worn, and (iii) the straps define a carriage extending from the girth; and
   (e) a heel pad cooperatively attached to the straps within the carriage.

2. The ankle brace of claim 1 wherein the ankle cover is effective for covering both ends of the malleolus of a wearer when the brace is worn.

3. The ankle brace of claim 1 wherein the ankle cover has a concave inner surface configured and arranged to accommodate a protruding end of the malleolus of the wearer.

4. The ankle brace of claim 2 wherein (i) the ankle cover defines first and second ankle cups configured and arranged to respectively cover first and second ends of the malleolus of a wearer when the brace is worn and (ii) each ankle cup has a concave inner surface configured and arranged to accommodate a protruding end of the malleolus.

5. The ankle brace of claim 1 wherein the first and second straps are inextensible.

6. The ankle brace of claim 1 wherein the first and second straps are continuous.

7. The ankle brace of claim 6 wherein the strap has a length and the length of the first and second straps are nonadjustable.

8. An in-the-shoe ankle brace, comprising:
   (a) a girth having first and second lateral ends and upper and lower longitudinal edges;
   (b) an adjustable fastening means cooperatively attached to the first and second lateral ends of the girth;
   (c) an ankle cover extending from the lower longitudinal edge of the girth having at least a portion positioned proximate the first lateral end of the girth;
   (d) a first strap and a second strap configured and arranged so as to be substantially parallel with each other, each strap extending from the lower longitudinal edge of the girth and having (i) a first end attached to the girth proximate the first lateral end of the girth, (ii) a second end attached to the girth proximate the second lateral end of the girth, and (iii) an intermediate length extending over the ankle cover; wherein the strap defines a carriage extending from the girth; and
   (e) a heel pad cooperatively attached to the strap within the carriage.

9. The ankle brace of claim 8 wherein the girth has a lateral length and the ankle cover extends substantially the entire lateral length of the girth.

10. The ankle brace of claim 8 wherein the ankle cover has a concave inner surface.

11. The ankle brace of claim 10 wherein (i) the ankle cover has first and second lateral ends, (ii) the cover defines a first ankle cup proximate the first lateral end of the cover, (iii) the cover defines a second ankle cup proximate the second lateral end of the cover, and (iv) both ankle cups have a concave inner surface.

12. The ankle brace of claim 8 wherein the first and second straps are inextensible.

13. The ankle brace of claim 8 wherein the first and second straps are continuous.

14. The ankle brace of claim 13 wherein the first and second straps have a length and the length of the strap is nonadjustable.

* * * * *